United States Patent [19]
Le Mitouard

[11] Patent Number: 5,429,683
[45] Date of Patent: Jul. 4, 1995

[54] FACE MASK FOR BREATHING

[76] Inventor: Anne Le Mitouard, 3 Allée du Parc de Choisy, 75013 Paris, France

[21] Appl. No.: 150,073
[22] PCT Filed: May 20, 1992
[86] PCT No.: PCT/FR92/00448
§ 371 Date: Nov. 22, 1993
§ 102(e) Date: Nov. 22, 1993
[87] PCT Pub. No.: WO92/20395
PCT Pub. Date: Nov. 26, 1992

[30] Foreign Application Priority Data

May 22, 1991 [FR] France ............... 91 06153

[51] Int. Cl.$^6$ ............................................. A62B 7/00
[52] U.S. Cl. ..................... 128/206.24; 128/205.25; 128/206.26; 128/207.11
[58] Field of Search .................. 128/205.25, 206.24, 128/206.25, 206.26, 203.22, 207.13, 206.28, 206.29, 206.27, 207.11

[56] References Cited

U.S. PATENT DOCUMENTS

| | | | |
|---|---|---|---|
| 2,133,699 | 10/1938 | Heidbrink | 128/206.24 |
| 2,313,999 | 3/1943 | Kreiselman | 128/206.26 |
| 2,353,643 | 7/1944 | Bulbulian | 128/207.11 |
| 2,391,677 | 12/1945 | Bulbulian | 128/207.11 |
| 2,917,045 | 12/1959 | Schildknecht et al. | |
| 3,052,887 | 9/1962 | Sockel et al. | 128/206.24 |
| 3,090,380 | 4/1963 | Dold | 128/203.11 |
| 3,167,070 | 1/1965 | Silverman | 128/206.24 |
| 3,695,264 | 10/1972 | Laeral | 128/206.26 |
| 4,559,940 | 12/1985 | McGinnis | 128/207.14 |
| 4,803,981 | 2/1989 | Vickery | 128/206.24 |
| 4,807,617 | 2/1989 | Nesti . | |

FOREIGN PATENT DOCUMENTS

| | | | |
|---|---|---|---|
| 552798 | 2/1958 | Canada | 128/206.24 |
| 602557 | 8/1960 | Canada | 128/206.24 |
| 644740 | 5/1937 | Germany | 128/206.24 |
| 1944548 | 3/1971 | Germany . | |
| 19022 | of 1899 | United Kingdom | 128/206.24 |
| 8803036 | 5/1988 | WIPO . | |

Primary Examiner—Edgar S. Burr
Assistant Examiner—William J. Deane, Jr.
Attorney, Agent, or Firm—Sixbey, Friedman, Leedom & Ferguson; Gerald J. Ferguson, Jr.; Tim L. Brackett

[57] ABSTRACT

A face mask, in particular for mechanically ventilating a patient, the mask comprising means interposed between a breathe-in/breathe-out pipe (10) and at least one of the nose and mouth orifices of the patient (5) to provide a sealed connection between the pipe and the respiratory tract of the patient, wherein said means comprise a thin shell (1) delimited by a substantially ovoid concave inside surface (7) whose apex is provided with an opening (2), a thick and flexible lining (6) suitable for engaging inside the shell (1) and projecting beyond said shell in the form of a sealing rim that deforms to match the shape of the portion of the face (5) that surrounds the opening to the respiratory tract, the lining having a tubular endpiece (8) suitable for being snap-fastened in the opening (2) of said shell (1) and forming a sleeve for connection to the pipe (10), the mask also having a harness (3, 4) for fixing it to the head of the user (5) and including straps that are fixed to the shell.

9 Claims, 2 Drawing Sheets

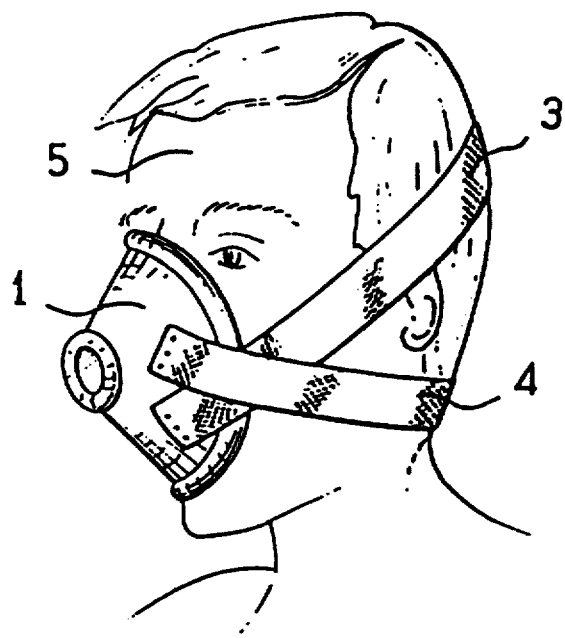
FIG_1
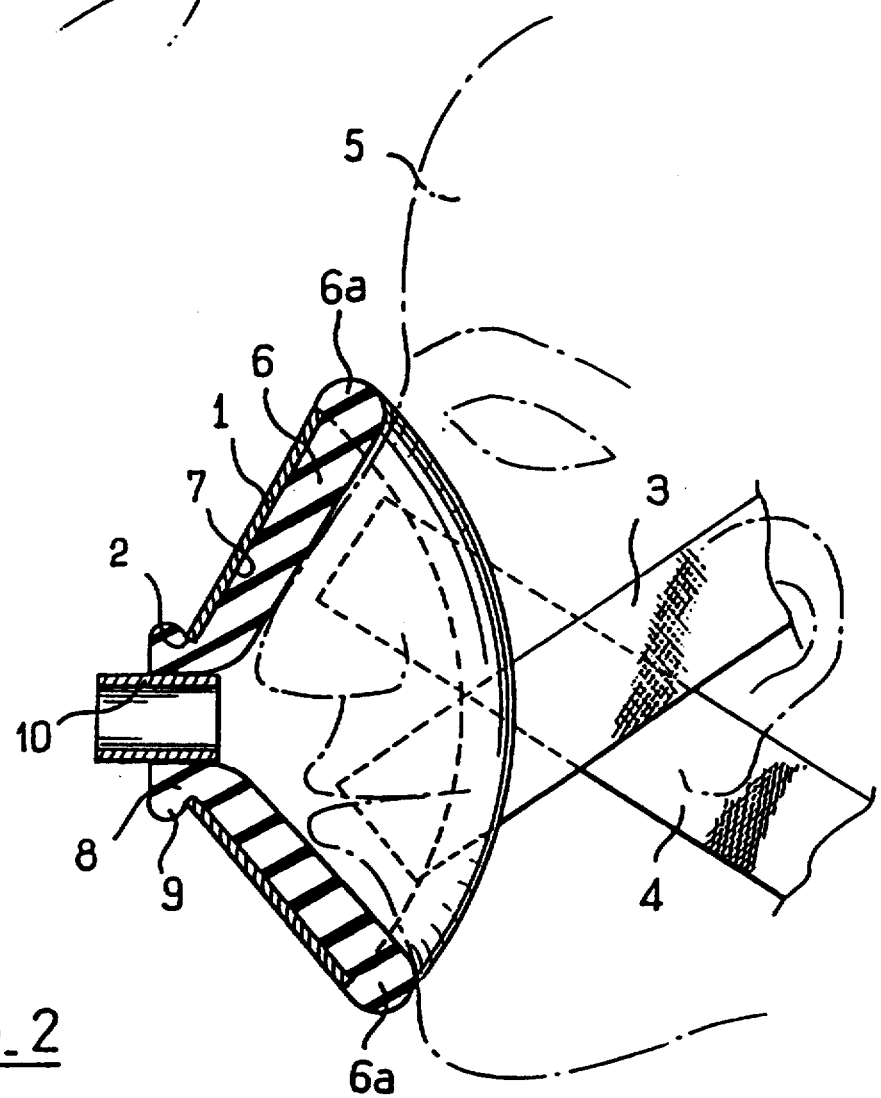
FIG_2

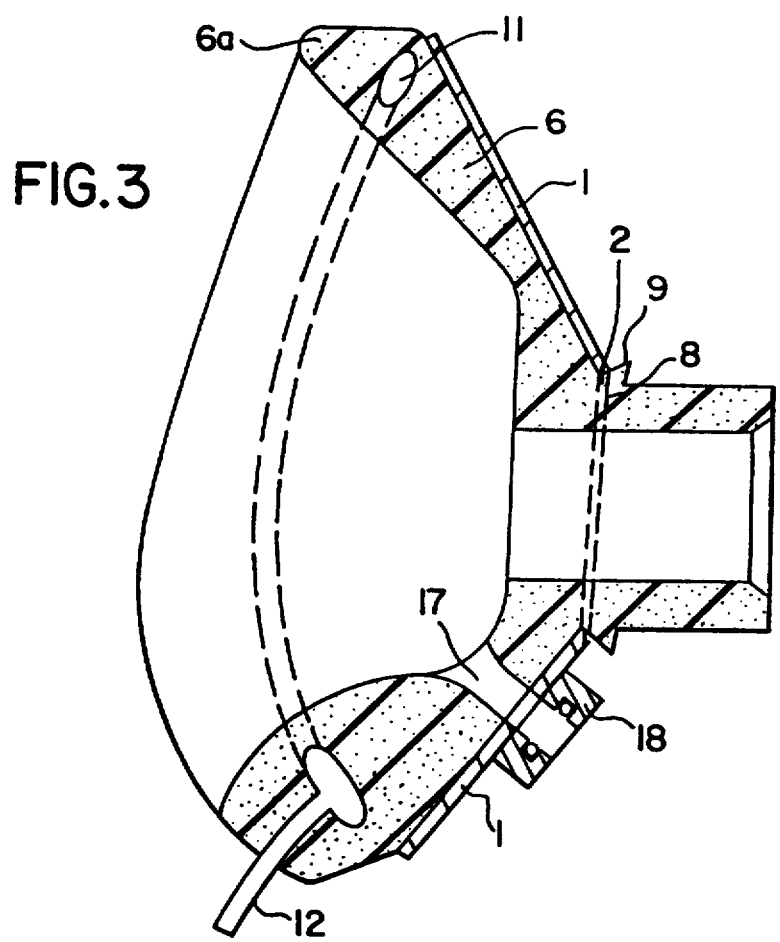
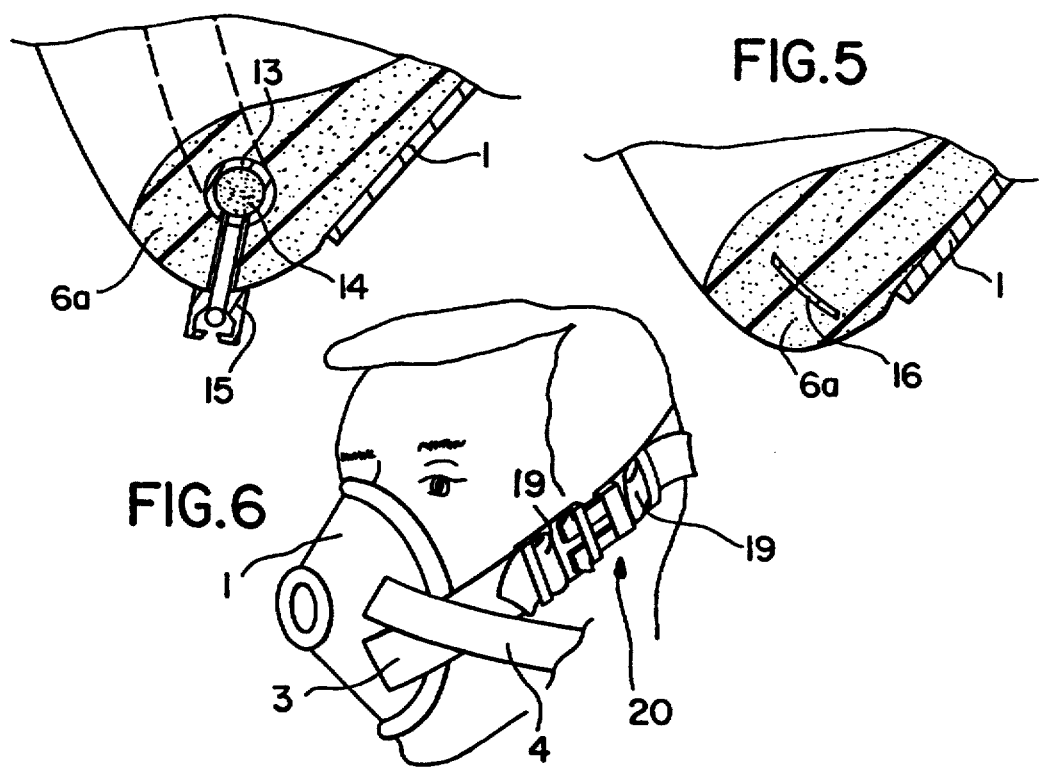

FACE MASK FOR BREATHING

The present invention relates to a face mask for breathing.

There is no point in listing the numerous circumstances in which a breathing mask is necessary. Nevertheless, one such circumstance is particularly important from the point of view of the constraints that it imposes: this is mechanically ventilating people suffering from temporary respiratory insufficiency, e.g. in the event of chronic or postoperative reanimation.

Until now, assisted ventilation for such people has mainly been achieved by inserting a tube into the trachea, which gives rise to numerous drawbacks. Firstly the probe inserted into the upper respiratory tract is a source of traumatism for the mucous membranes with which it comes into contact. It also constitutes a considerable impediment for the patient who cannot speak and who therefore cannot communicate easily with the outside. Finally, it can be the source of complications (tracheal, pleuropulmonary, or ENT, . . . superinfection).

Several attempts have already been made to use a gentler method implementing a mask to replace that invasive technique. The masks presently available are not entirely satisfactory, either because they provide inadequate sealing with the face (leaks take place in general beneath the eyes, thus running the risk of conjunctivitis), or else because contact between the mask and the face gives rise to allergy or to traumatism at compression points which means that prolonged wearing is not possible and is detrimental to the comfort of the patient.

Proposals have also been made for masks that are modelled directly on the face of the patient by means of a malleable material that is shaped between the face and a pipe coupling for connection to the hose delivering the gaseous mixture, with the material fitting closely over the shape of the face. Such equipment suffers from the drawback of being lengthy to install which can sometimes be totally incompatible with the need for urgency.

The present invention seeks to mitigate the above drawbacks by means of a mask that is simple in structure and that can be put into operation very quickly, which is comfortable because it is light in weight and because it adapts closely to the shape of the face, and which also satisfies the relevant requirements for sterility and asepsis.

To this end, the present invention thus provides a face mask, in particular for mechanically ventilating a patient, the mask comprising means interposed between a breathe-in/breathe-out pipe and at least one of the nose and mouth orifices of the patient to provide a sealed connection between the pipe and the respiratory tract of the patient. According to the invention, said means comprise a thin shell delimited by a substantially ovoid concave inside surface whose apex is provided with an opening, a thick and flexible lining suitable for engaging inside the shell and projecting beyond said shell in the form of a sealing rim that deforms to match the shape of the portion of the face that surrounds the opening to the respiratory tract, the lining having a tubular endpiece suitable for being snap-fastened in the opening of said shell and forming a sleeve for connection to the pipe, the mask also having a harness for fixing it to the head of the user and including straps that are fixed to the shell.

Other characteristics and advantages appear from the following description of a particular embodiment.

Reference is made to the accompanying drawings, in which:

FIG. 1 is a diagrammatic outside view of a mask of the invention applied to the face of a user;

FIG. 2 is a median section through the mask;

FIGS. 3, 4, and 5 are fragmentary section views showing variant embodiments of a mask in which the flexible lining possesses a reinforcing member for shaping purposes; and FIG. 6 shows means for buckling the harness that are separate from the means for fixing the straps to the shell.

With reference to the figures, it can be seen that the mask of the invention comprises a shell 1 made of a thin plastics material by injection, thermoforming, or any other suitable manner so as to have a shape that is substantially conical or somewhat ovoid. The narrowest portion of the shell is designed to receive the bony portion of the ridge of the nose while the wider bottom portion bears against the anterior portion of the lower jaw. The material used has a degree of elastic flexibility so as to be able to deform slightly when the mask is applied against the face of a patient. The apex of the shell is provided with a substantially circular opening 2. The outside face thereof is fitted with means for securing the ends of straps 3 and 4 of a harness for fixing the mask to the face of the patient: 5. The straps can be fixed to the shell by any conventional means (gluing, stapling, . . . ) or by means of bars (not shown) integrally formed with the shell and round which the straps are fixed. Together with the shell, the straps form loops that may be open or closed and that may be elastic or non-elastic, and that enable the force with which the mask is pressed against the face of the patient to be adjusted and/or modified. Preferably, the ends of one of the straps, referred to as the "upper" strap since it passes closer to the top of the head, are connected to lower lateral zones of the mask, i.e. zones beneath the opening 2, whereas the ends of the other strap, referred to as the "lower" strap since it passes round the nape of the neck, are connected to the shell in upper side zones, i.e. above the opening 2. The straps of the harness cross over near to the shell. This disposition makes it possible to optimize the way in which forces pressing the mask against the face of the patient are distributed.

The inside surface of the shell 1 receives a lining 6 whose outside surface is complementary in shape to the inside surface 7 of the shell 1 so as to fit snugly thereagainst. The lining is made of a flexible material, e.g. a polyurethane foam covered in latex. This material has the advantage of being very well accepted by the patient. If there are allergy problems, the skin of the lining may be provided with a silicone coating. The lining is fixed to the shell of the mask by means of a tubular endpiece 8 integrally formed with the lining and inserted through the opening 2. The endpiece 8 is held in the opening 2 by elastic deformation of the endpiece, and this is reinforced by a snap-fastening rim 9 that locks the endpiece in place.

The lining installed in the shell in this way performs several kinds of function. Firstly, the lining constitutes a kind of relatively thick cushion that provides sealing by being pressed against and by projecting slightly beyond the outside of the shell in the form of a rim 6a that is capable of being deformed by the force with which the edge of the mask shell presses against the face, thereby ensuring continuity of contact. The good quality of this contact makes it possible to contain a positive ventilation pressure of as much as 25 millibars. The lining also constitutes a material for filling the shell, thereby making it possible to minimize the dead space inside the mask. The tubular endpiece for fixing the lining to the shell also receives the end of a breathe-in/breathe-out pipe 10 with the pipe being held in place by friction and with the connection being sealed by the lining. A screw thread or a series of notches may be provided between the pipe and the endpiece.

One of the major advantages of this structure lies in the fact that the lining is very easily separated from the shell and can thus be discarded after each use. It is thus possible to have a single model of shell and to fit a range of models of lining therein as a function of the shape of the patient. The shell can be reused since it is easy to sterilize. The pipe is connected to the mask in a manner that is highly simplified while still being proof against untimely disconnection.. Finally, the mask of the invention is extremely light in weight, and this constitutes a non-negligible comfort factor.

It should also be observed that the mask described above may be implemented in various different ways, some of which are shown in FIGS. 3 to 6. Some of the elements described above are shown again in these figures under the same references.

FIGS. 3 to 5 show a mask in which the foam 6 includes means in the vicinity of the rim 6a for improving the shaping of the rim to match the shape of the face against which it is applied. These means are of the type comprising a reinforcing member that can be deformed between two states. In FIG. 3, the reinforcing member is a tubular chamber 11 embedded in the foam 6 and suitable for filling with a settable material by means of an endpiece 12. The wall of this chamber is deformable without being elastic, so the cross-section of the chamber is not constant. The larger section portions are situated over concave regions of the face (beside the nose, for example) while the smaller section portions thereof are situated over convex regions of the face (e.g. over the cheek bones). By inserting a gaseous or liquid fluid (or even a settable fluid) into said tubular chamber, modulated thrust of the foam against the face is obtained with the magnitude of the thrust being directly related to the section of the chamber. If the fluid sets, then there is no need to close the endpiece 12 in sealed manner. The mask can thus be personalized.

In FIG. 4, the reinforcing member is constituted by a tubular sheath 13 filled with a divided material or powder 14. When the mask is put into place, the foam can be moved by hand so as to fit closely over the surface of the face. Once deformed in this way together with the foam, the sheath 13 is evacuated via an endpiece 15 that is fitted with a non-return valve, thereby stiffening the sheath so that it conserves the shape that has been imparted to it.

In FIG. 5, the reinforcing member is constituted by a metal insert 16 in the form of a wire or tape that can be deformed by hand and that retains such deformation, thereby personalizing the shape of the rim 6a.

It may also be observed that the mask shown in FIG. 3 has a secondary orifice 17 with a guiding and sealing endpiece 18 enabling a probe, e.g. a gastric probe, to be passed therethrough thus avoiding any need to pass such a probe between the face and the rim which would give rise to leakage.

In a variant that is not shown, the shell 1 may have a transparent portion, e.g. level with the orifice 17, constituting a window for inspecting the inside of the mask when it is in use on a patient. The foam 16 should possess a corresponding cutout overlying the window.

Finally, FIG. 6 shows a practical disposition for the harness 3, 4. The straps 3 and 4 include conventional means 19 for adjusting their lengths, which means include buckles in the form of clips 20 having resilient tongues. Such a disposition makes it possible to adjust the fixing harness on a single occasion with the adjustment then being conserved even when the harness is opened.

The straps 3 and 4 may be permanently fixed to the shell 1 by any conventional means, or they may merely be coupled to said shell by releasable fastening means textiles having shapes that co-operate).

The invention has been described in its application to a breathing mask for covering the mouth and the nose. It is also applicable to a mask for covering the nose only, in which case the mask bears against the upper jaw between the nose and the mouth. In other applications, the endpiece may merely constitute a support for a readily interchanged filter for filtering particles or chemicals.

I claim:

1. A face mask, in particular for mechanically ventilating a patient, the mask comprising means interposed between a breath-in/breath-out pipe and at least one of the nose and mouth orifices of the patient to provide a sealed connection between a breath-in/breath-out pipe and the respiratory tract of the patient, said means having a thin shell delimited by a substantially ovoid concave inside surface whose apex is provided with an opening, a thick and flexible lining engaging the inside of the shell and projecting beyond said shell to form a sealing rim that deforms to match the shape of the portion of the face that surrounds the opening to the respiratory tract and a harness for fixing said face mask to the head of the user and including straps that are fixed to the shell, wherein said lining has a tubular endpiece projecting through the opening of said shell and forming a sleeve for connection to a breath-in/breath-out pipe.

2. A mask according to claim 1, characterized in that the thick and flexible lining includes a reinforcement member in its rim forming portion, the reinforcement member being suitable for being deformed to fit the shape of the face.

3. A mask according to claim 2, characterized in that said reinforcement member is constituted by a deformable metal wire.

4. A mask according to claim 2, characterized in that the reinforcement member is constituted by a inflatable tubular chamber of variable section.

5. A mask according to claim 2, characterized in that the reinforcement member is constituted by a tubular envelope filled with a divided material and suitable for being evacuated.

6. A mask according to claim 1, characterized in that the lining is constituted by a synthetic material in the form of a foam.

7. A mask according to claim 1, characterized in that the endpiece of the lining includes a rim at its end that forms a snap-fastening catch for engaging the lining on the shell.

8. A mask according to claim 1, characterized in that the fixing harness comprises an upper strap whose ends are fixed to the shell in two symmetrical lateral zones situated beneath the level of the opening, and a lower strap whose ends are secured to the shell in two symmetrical lateral zones situated above the level of the opening, 9. A mask according to claim 8, characterized in that each strap of the harness includes means for adjusting its length and buckle means that are independent of the adjustment means.

* * * * *